(12) United States Patent
Hickey et al.

(10) Patent No.: US 8,936,927 B2
(45) Date of Patent: Jan. 20, 2015

(54) PROCESSES FOR STARTING UP DEEP TANK ANAEROBIC FERMENTATION REACTORS FOR MAKING OXYGENATED ORGANIC COMPOUND FROM CARBON MONOXIDE AND HYDROGEN

(75) Inventors: Robert Hickey, Okemos, MI (US); Richard E. Tobey, St. Charles, IL (US); Shih-Perng Tsai, Naperville, IL (US)

(73) Assignee: Coskata, Inc., Warrenville, IL (US)

( * ) Notice: Subject to any disclaimer, the term of this patent is extended or adjusted under 35 U.S.C. 154(b) by 492 days.

(21) Appl. No.: 13/243,159

(22) Filed: Sep. 23, 2011

(65) Prior Publication Data
US 2013/0078693 A1    Mar. 28, 2013

(51) Int. Cl.
| | | |
|---|---|---|
| C12P 5/00 | (2006.01) |
| C12P 7/06 | (2006.01) |
| C12M 1/00 | (2006.01) |
| C12M 1/34 | (2006.01) |

(52) U.S. Cl.
CPC C12P 7/06 (2013.01); C12M 29/06 (2013.01); C12M 41/32 (2013.01); Y02E 50/17 (2013.01); Y10S 435/801 (2013.01)
USPC .............. 435/245; 435/801; 585/240

(58) Field of Classification Search
CPC .............. C12P 1/00; C12P 5/002; C12P 7/00; C12P 7/04; C12P 7/06; C12P 7/065; C12P 7/16; C12M 21/00; C12M 21/12; C12M 27/00; C12M 27/04; C12M 29/00; C12M 29/06
See application file for complete search history.

(56) References Cited

U.S. PATENT DOCUMENTS

| | | | |
|---|---|---|---|
| 4,162,970 | A | 7/1979 | Zlokarnik et al. |
| 4,426,450 | A | 1/1984 | Donofrio |
| 6,193,220 | B1 | 2/2001 | Kelly |
| 7,285,402 | B2 | 10/2007 | Gaddy et al. |
| 7,704,723 | B2 | 4/2010 | Huhnke et al. |
| 2003/0211585 | A1 | 11/2003 | Gaddy et al. |
| 2008/0305539 | A1 | 12/2008 | Hickey et al. |
| 2009/0215139 | A1 | 8/2009 | Datta et al. |
| 2011/0059499 | A1 | 3/2011 | Simpson et al. |

OTHER PUBLICATIONS

Datar, R.P. et al. 2004. Fermentation of Biomass-Generated Producer Gas to Ethanol. Biotechnology and Bioengineering 86(5):587-594. specif. pp. 587, 590-593.*
Grethlein, A.J. 1991. Metabolic engineering of product formation during carbon monoxide fermentation by Butyribacterium methylotrophicum. Ph.D. Dissertation, Dept. of Chemical Engineering, Michigan State Univ. pp. 1-217. specif. pp. 6, 57, 75.*
U.S. Appl. No. 12/826,991, filed Jun. 30, 2010, Hickey et al.
Munasinghe, et al., Biomass-derived Syngas Fermentation in Biofuels: Opportunities and Challenges, Biosource Technology, 101 (2010) 5013-5022.
Munasinghe, et al., Syngas Fermentation to Biofuel: Evaluation of Carbon Monoxide Mass Transfer Coefficient (kLa) in Different Reactor Configurations, Biotechol. Prog., 2010.
Bredwell, et al., in Reactor Design Issues for Synthesis-Gas Fermentations, Biotechnol. Prog., 15 (1999) 834-844.
Xu, et al., The effects of syngas impurities on syngas fermentation to liquid fuels, Biomass and Bioenergy, 35, (2011), 2690-2696.
Krishna, et al., Influence of alcohol addition on gas hold-up in bubble columns: development of a scale up model, Int. Comm. Heat Mass Transfer, 27 No. 4, (2000) 465-472.
Wilkins, et al., Microbial production of ethanol from carbon monoxide, Current Opinion in Biotechnology, 22 (2011), 326-330, production.
Ahmed, et al., Fermentation of Biomass-Generated Synthesis Gas: Effects of Nitric Oxide, Biotechnology and Bioengineering, 97, No. 5, (2007), 1080-1086.
Abubackar, et al., Biological conversion of carbon monoxide: rich syngas or waste gas to bioethanol, Biofuels, Bioproducts & Biorefining, 5 (2011), 93-114.

* cited by examiner

Primary Examiner — John S Brusca
Assistant Examiner — Sharon M Papciak

(57) ABSTRACT

Processes are provided for starting up of anaerobic, deep tank fermentation systems used in the anaerobic bioconversion of hydrogen and carbon monoxide in a gaseous substrate stream to oxygenated organic compounds such as ethanol. In the processes injectors using a motive liquid are used to introduce gas substrate into the deep tank fermentation reactor where at least one of:
  (i) adjusting the gas to liquid flow ratio through an injector,
  (ii) changing the rate of liquid flow through an injector, and
  (iii) adjusting the carbon monoxide mole fraction in the gas feed by admixture with at least one other gas,
wherein the mass transfer of carbon monoxide to an aqueous menstruum in the reactor is controlled to obtain the robust growth of the microorganism while maintaining the carbon monoxide concentration below that amount which is unduly adverse to the microorganism. In preferred aspects of the invention, recycled gas from the head space of the reactor is used to modulate the supply of carbon monoxide to the aqueous menstruum.

20 Claims, 3 Drawing Sheets

PROCESSES FOR STARTING UP DEEP TANK ANAEROBIC FERMENTATION REACTORS FOR MAKING OXYGENATED ORGANIC COMPOUND FROM CARBON MONOXIDE AND HYDROGEN

FIELD OF THE INVENTION

This invention pertains to processes for starting up anaerobic, deep tank fermentation systems used in the anaerobic bioconversion of hydrogen, carbon monoxide and carbon dioxide in a gaseous substrate stream to oxygenated organic compounds such as ethanol.

BACKGROUND

Anaerobic fermentations of hydrogen and carbon monoxide involve the contact of the substrate gas in a liquid fermentation menstruum with microorganisms capable of generating oxygenated organic compounds such as ethanol, acetic acid, propanol and n-butanol. The production of these oxygenated organic compounds requires significant amounts of hydrogen and carbon monoxide. For instance, the theoretical equations for the conversion of carbon monoxide and hydrogen to ethanol are:

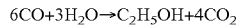

$6CO + 3H_2O \rightarrow C_2H_5OH + 4CO_2$

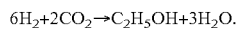

$6H_2 + 2CO_2 \rightarrow C_2H_5OH + 3H_2O.$

As can be seen, the conversion of carbon monoxide results in the generation of carbon dioxide. The conversion of hydrogen involves the consumption of hydrogen and carbon dioxide, and this conversion is sometimes referred to as the $H_2/CO_2$ conversion. For purposes herein, it is referred to as the hydrogen conversion.

Typically the substrate gas for carbon monoxide and hydrogen conversions is, or is derived from, a synthesis gas (syngas) from the gasification of carbonaceous materials, from the reforming of natural gas and/or biogas from anaerobic digestion or from off-gas streams of various industrial methods. The gas substrate contains carbon monoxide, hydrogen, and carbon dioxide and usually contains other components such as water vapor, nitrogen, methane, ammonia, hydrogen sulfide and the like. (For purposes herein, all gas compositions are reported on a dry basis unless otherwise stated or clear from the context.)

These substrate gases are typically more expensive than equivalent heat content amounts of fossil fuels. Hence, a desire exists to use these gases efficiently to make higher value products. The financial viability of any conversion process, especially to commodity chemicals such as ethanol and acetic acid, will be dependent upon capital costs, the efficiency of conversion of the carbon monoxide and hydrogen to the sought products and the energy costs to effect the conversion.

Syngas fermentation processes suffer from the poor solubility of the gas substrate, i.e., carbon dioxide and hydrogen, in the liquid phase of the fermentation menstruum where the biological processes occur. Munasinghe, et al., in *Biomass-derived Syngas Fermentation in Biofuels: Opportunities and Challenges, Biosource Technology*, 101 (2010) 5013-5022, summarize volumetric mass transfer coefficients to fermentation media that are reported in the literature for syngas and carbon monoxide in various reactor configurations and hydrodynamic conditions. A number of conditions can enhance the mass transfer of syngas to the liquid phase. For instance, increasing the interfacial area between the gas feed and the liquid phase can improve mass transfer rates.

Numerous processes have been disclosed for the conversion of carbon monoxide and hydrogen to oxygenated compounds. One such process suspends the microorganisms for the conversion in an aqueous menstruum contained in a stirred tank reactor such as by using a motor driven impeller. Stirred tank fermentation reactors provide many advantages. For stirred tank reactors, increasing the agitation of the impeller is said to improve mass transfer as smaller bubble sizes are obtained. Also, the stirring action not only distributes the gas phase in the aqueous menstruum but also the duration of the contact between the phases can be controlled. Another very significant benefit is that the composition within the stirred tank can be relatively uniform. For instance, Munasignhe, et al., in a later published paper, *Syngas Fermentation to Biofuel: Evaluation of Carbon Monoxide Mass Transfer Coefficient ($k_La$) in Different Reactor Configurations, Biotechol. Prog.*, 2010, Vol. 26, No. 6, pp 1616-1621, combine a sparger (0.5 millimeter diameter pores) with mechanical mixing at various rotational rates to provide enhanced mass transfer. This uniformity enables good control of the fermentation process during steady-state operation. This is of particular advantage in the anaerobic conversion of carbon monoxide and hydrogen to oxygenated compounds where two conversion pathways exist. Hence the carbon dioxide generated from the conversion of carbon monoxide is proximate in location to the hydrogen consumption pathway that consumes carbon dioxide. The uniformity further facilitates the addition of fresh gas substrate. The problems with stirred tank reactors are capital costs, the significant amount of energy consumed in the needed mixing and agitation, and the need for plural stages to achieve high conversion of substrate.

Bredwell, et al., in *Reactor Design Issues for Synthesis-Gas Fermentations*, Biotechnol. Prog., 15 (1999) 834-844, disclose using microbubble sparging with mechanical agitation. At page 839 they state:

"When microbubble sparging is used, only enough power must be applied to the reactor to provide adequate liquid mixing. Thus axial flow impellers designed to have low shear and a high pumping capacity would be suitable when microbubbles are used in stirred tanks."

They conclude by stating:

"An improved ability to predict and control coalescence rates is needed to rationally design commercial-scale bioreactors that employ microbubble sparging." (p. 841)

Another type of fermentation apparatus is a bubble column fermentation reactor wherein the substrate gas is introduced at the bottom of the vessel and bubbles through the aqueous menstruum ("bubble reactor"). See Munasinghe, et al., in *Biomass-derived Syngas Fermentation in Biofuels: Opportunities and Challenges, Biosource Technology*, 101 (2010) 5013-5022. In order to achieve sought mass transfer from the gas to liquid phases, workers have provided the gas feed to bubble columns in the form of microbubbles. The authors report that in one study, the mass transfer obtained for a bubble column reactor was higher than that for a stirred tank reactor mainly due to the higher interfacial surface area obtained with the bubble column reactor. Advantageously, commercial-scale bubble column fermentation reactors are relatively simple in design and construction and require relatively little energy to operate.

In co-pending U.S. patent application No. 13/243,426, filed on even date herewith, processes are disclosed for enhancing the performance of large-scale, anaerobic fermentors. In these processes, a reactor having an aqueous menstruum depth of at least about 10 meters is used, and gas feed is supplied to the aqueous menstruum in the form of a stable gas-in-liquid dispersion. The aqueous menstruum is mechanically stirred at a rate sufficient to provide relatively uniform liquid phase composition within the aqueous menstruum without unduly adversely affecting the gas-in-liquid dispersion. For purposes herein, this is referred to as a mechanically-assisted liquid distribution tank reactor, or MLD tank reactor. At least a portion of the off-gas from the aqueous menstruum is recycled to obtain a molar conversion efficiency of total hydrogen and carbon monoxide in the gas substrate to oxygenated organic compound of at least about 80 percent in a single reactor stage. Accordingly, capital cost savings and energy savings over a conventional stirred tank reactor can be obtained.

For purposes herein, both deep, bubble column fermentation reactors and the large-scale MLD tank reactors supplied with stable gas feed-in-liquid dispersions and using low stifling rates, are referred to as deep tank reactors.

Deep tank reactors using microbubbles can provide economically attractive facilities for anaerobic conversion of syngas to oxygenated organic compound, but difficulties are present. In their earlier review article, Munasignhe, et al., report that the gas-liquid mass transfer is the major resistance for gaseous substrate diffusion. The authors state at page 5017:

"High pressure operation improves the solubility of the gas in the aqueous phase. However, at higher concentrations of gaseous substrates, especially CO, anaerobic microorganisms are inhibited."

Other workers have understood that the presence of excess carbon monoxide can adversely affect the microorganisms and their performance. See paragraphs 0075 through 0077 and 0085 though 0086 of United States published patent application No. 20030211585 (Gaddy, et al.) disclosing a continuously stirred tank bioreactor for the production of ethanol from microbial fermentation. At paragraph 0077, Gaddy, et al., state:

"The presence of excess CO unfortunately also results in poor $H_2$ conversion, which may not be economically favorable. The consequence of extended operation under substrate inhibition is poor $H_2$ uptake. This eventually causes cell lysis and necessary restarting of the reactor. Where this method has an unintended result of CO substrate inhibition (the presence of too much CO for the available cells) during the initial growth of the culture or thereafter, the gas feed rate and/or agitation rate is reduced until the substrate inhibition is relieved."

At paragraph 0085, Gaddy, et al., discuss supplying excess carbon monoxide and hydrogen. They state:

"A slight excess of CO and $H_2$ is achieved by attaining steady operation and then gradually increasing the gas feed rate and/or agitation rate (10% or less increments) until the CO and $H_2$ conversions just start to decline."

For deep tank reactors, the height of the aqueous menstruum is a primary determinant of the contact time for the bioconversion to occur. This height also is a determinant of the static head at the bottom portion of the reactor. Higher pressures result in smaller bubble sizes and higher partial pressures both of which enhance mass transfer efficiency and gas substrate conversion efficiency in the fermentation reactor. Thus, on a commercial scale, deep tank reactors have a depth of at least about 10, preferably at least about 15, meters and use microbubbles of gas feed in order to achieve molar conversion efficiencies of at least about 60 percent of the total hydrogen and carbon monoxide supplied to the reactor. However, these operating parameters increase the risk of carbon monoxide inhibition.

The risk of carbon monoxide inhibition in deep tank reactors is more pronounced in start-up. Typically at start-up, the reactor is supplied with a culture of microorganisms from a seed farm and the size of the culture is limited, usually to about 10 percent or less of the concentration of the culture in the reactor at steady state. The reactor is then operated to obtain a robust growth of the culture to the sought density for steady state operation. The very dilute culture concentration is more subject to damage than would be the denser culture at steady state. Especially with commercial scale reactors, i.e., those with liquid capacities of at least 1 million, and more often at least about 5, say, 5 to 25, million, liters, sufficient culture volume to completely fill the capacity of the reactor is generally unavailable. Consequently, the reactor can be only partially filled with aqueous menstruum and the culture must be grown first to increase density in that portion filled. Then additional liquid is added to the reactor, and the culture must undergo further growth to viable densities. This process is continued until the deep tank reactor has reached its sought capacity.

To reduce the time required for start-up, it is desired to provide sufficient substrate to the microorganisms for robust growth. However, to reduce risks of overdosing the microorganisms with carbon monoxide, a common practice has been to undersupply gas substrate during start-up and thus extend the duration of the start-up process.

Processes are therefore sought to capture the benefits provided by a deep tank fermentation system at steady state conditions yet be able to rapidly start-up the deep, tank reactor without undue risk of damage to the microorganism culture.

SUMMARY OF THE INVENTION

In accordance with this invention, a deep tank fermentation reactor for the anaerobic bioconversion of a gas substrate comprising carbon monoxide, hydrogen and carbon dioxide in an aqueous menstruum containing microorganisms suitable for converting said substrate to oxygenated organic compound is started up using an initial low height of aqueous menstruum in the reactor and at least one injector using a motive liquid to modulate the supply gas feed to the aqueous menstruum to provide robust growth of the culture of microorganisms while reducing the risk of carbon monoxide inhibition. The modulating of the supply of gas feed is accomplished by adjusting the gas to liquid flow ratio and the rate of liquid flow to the injector and by adjusting the mole fraction of carbon monoxide in the gas feed by admixture with at least one other gas. The motive liquid also provides a force to cause currents in the aqueous menstruum to reduce the risk of localized over supply of carbon monoxide.

In one broad aspect, the processes of this invention for starting-up a deep tank reactor for the anaerobic bioconversion of a gas substrate comprising carbon monoxide, hydrogen and carbon dioxide in an aqueous menstruum containing microorganisms suitable for converting said substrate to oxygenated organic compound comprise:

a. blanketing said reactor above the aqueous menstruum in a head space with at least one of carbon dioxide, nitrogen, and lower alkane to the essential exclusion of oxygen;

b. initially providing aqueous menstruum in the reactor to a depth less than about 10 meters, preferably less than about 7 meters, and sometimes less than about 5 meters, said aqueous menstruum being under fermentation conditions and having a concentration of said microorganisms of between about 0.03 and 3 grams per liter;

c. continuously supplying gas feed to a bottom portion of the reactor, said gas feed being at a rate sufficient to increase the concentration of microorganisms, said gas feed comprising said gas substrate to a bottom portion of said reactor via at least one injector, preferably 2 or more injectors, using a motive liquid, preferably derived from the aqueous menstruum, to form microbubbles having a diameter of less than about 500 microns, preferably between about 20 and 300 microns; and d. increasing intermittently or continuously the volume of aqueous menstruum in said reactor to the desired capacity while increasing the concentration of microorganisms to between 3 and 500 times that in step (b), preferably to between about 1 and 10 grams per liter, wherein by at least one of:
(i) adjusting the gas to liquid flow ratio through an injector,
(ii) changing the rate of liquid flow through an injector, and
(iii) adjusting the carbon monoxide mole fraction in the gas feed by admixture with at least one other gas,
the mass transfer of carbon monoxide to the aqueous menstruum in the reactor is modulated to obtain the growth of step (c) but maintains a carbon monoxide concentration in the aqueous menstruum below that amount which results in carbon monoxide inhibition.

It is not essential that the initial stages of start-up be conducted using microbubbles. Due to the reduced volume of aqueous menstruum at the initiation of start-up and often a low microorganism concentration, typically little oxygenated organic compound is capable of being produced. Thus, the mass transfer rates of carbon monoxide and hydrogen are not as economically important as they are at later stages of the start-up. Accordingly, in one aspect of the invention, a portion to essentially all of the gas feed may be supplied as bubbles greater than about 500 microns, e.g., from about 1 to 5 microns. However, the later stages of the start-up processes of this invention at least about 25, preferably at least about 50, volume percent of the gas feed is supplied in the form of microbubbles, especially after the height of the aqueous menstruum in the deep tank reactor is at least about 8, often at least about 5, meters.

In a preferred aspect of the processes of the invention, during the initial phases of the start-up process, the height of the aqueous menstruum is sufficiently low that the injectors can be used under venturi like conditions to allow recycle of the headspace gas. If desired, a blower may be used to facilitate achieving a desired flow rate of recycling head space gas.

The injectors may be of any suitable design. Jet injectors, especially slot injectors, are generally preferred, particularly as greater aqueous menstruum heights are achieved in the start-up process. Slot injectors have a high turn down ratio with respect to the motive liquid flow rate per injector used while still providing good microbubble formation. In general, the average bubble diameter decreases as the rate of motive liquid flow is increased. The smaller microbubbles have a higher surface area per unit volume which tends to increase the mass transfer rate of gas from the microbubble to the surrounding liquid, all other things remaining equal. Increasing motive liquid flow rate through the injectors also tends to increase agitation that enhances the axial mixing of the microbubbles in the reactor, especially at lower aqueous menstruum levels used at the commencement of start-up. By modulating the liquid and gas flow rates to the slot injectors it is also possible to generate larger bubbles, e.g., having diameters in excess of 1 millimeter, to enhance mixing of the aqueous menstruum. Additionally, the modulation enables a microbubble size to be generated that results in a stable gas-in-water dispersion.

In preferred aspects of the processes of this invention, the gas feed comprises gas recycled from the head space and the recycled gas is used as a modulating gas. This mode of modulation may be used to control the mole fraction of carbon monoxide in the gas feed provided by one or more injectors. The recycled gas may comprise essentially all of the gas feed provided by one or more injectors and provide a modulating effect on the concentration of carbon monoxide dissolved in the aqueous menstruum. The composition of the gas in the head space will change as the start-up process proceeds. For example, where the blanketing gas in the head space is initially nitrogen or carbon dioxide, as the process proceeds, unreacted carbon monoxide, hydrogen and co-product carbon dioxide from the conversion of carbon monoxide to oxygenated organic compound will enter the head space. Thus, the recycled gas will become a source of gas substrate for the gas feed. Hence, as the culture grows, the recycle gas can provide a gas feed with a lower mole fraction of carbon monoxide than that of the substrate gas and thereby provide a modulating effect. This recycle advantageously increases the conversion efficiency of the carbon monoxide and hydrogen contained in the fresh feed.

In another preferred aspect of the processes of this invention, at least two injectors are used and are sequenced with respect to the density of the culture in the aqueous menstruum and the height of the aqueous menstruum, i.e., the available contact time between the gas and liquid phases in the reactor. By sequencing, an injector may be off or may have a different composition gas feed than another injector or may have a different motive liquid feed rate than another injector or may have a different gas feed to motive liquid feed ratio than another injector.

In another broad aspect, the processes of this invention for starting-up a deep tank reactor for the anaerobic bioconversion of a gas substrate comprising carbon monoxide, hydrogen and carbon dioxide in an aqueous menstruum containing microorganisms suitable for converting said substrate to oxygenated organic compound comprise:

a. blanketing said reactor above the aqueous menstruum in a head space with at least one of carbon dioxide, nitrogen, and lower alkane to the essential exclusion of oxygen;

b. continuously supplying gas feed to a bottom portion of said reactor, said gas feed being at a rate sufficient to increase the concentration of microorganisms, said gas feed comprising said gas substrate to a bottom portion of said reactor via at least one injector, preferably 2 or more injectors, using a motive liquid, preferably derived from the aqueous menstruum, to form microbubbles having a diameter of less than about 500 microns, preferably between about 20 and 300 microns; and c. operating in substantially a liquid retention mode until the concentration of microorganisms is between 3 and 500 times that in step (b), preferably to between about 1 and 10 grams per liter.

A liquid retention mode connotes an operation of the reactor where substantially no aqueous menstruum is withdrawn from the reactor for purposes of a product stream or purge. Preferably the concentration of the oxygenated organic compound in the aqueous menstruum is maintained below that which unduly adversely affects the rate of growth of the culture of microorganisms. Preferably, the volume of the aqueous menstruum is increased during the start-up, and the concentration of the oxygenated organic compound is maintained below that which unduly adversely affects the rate of growth of the culture of microorganisms by intermittently or continuously increasing the volume of the aqueous menstruum in the reactor.

As discussed above, the initial stages of the start-up may comprise supplying the gas feed as bubbles larger than microbubbles.

DETAILED DISCUSSION

Definitions

Figure 1:
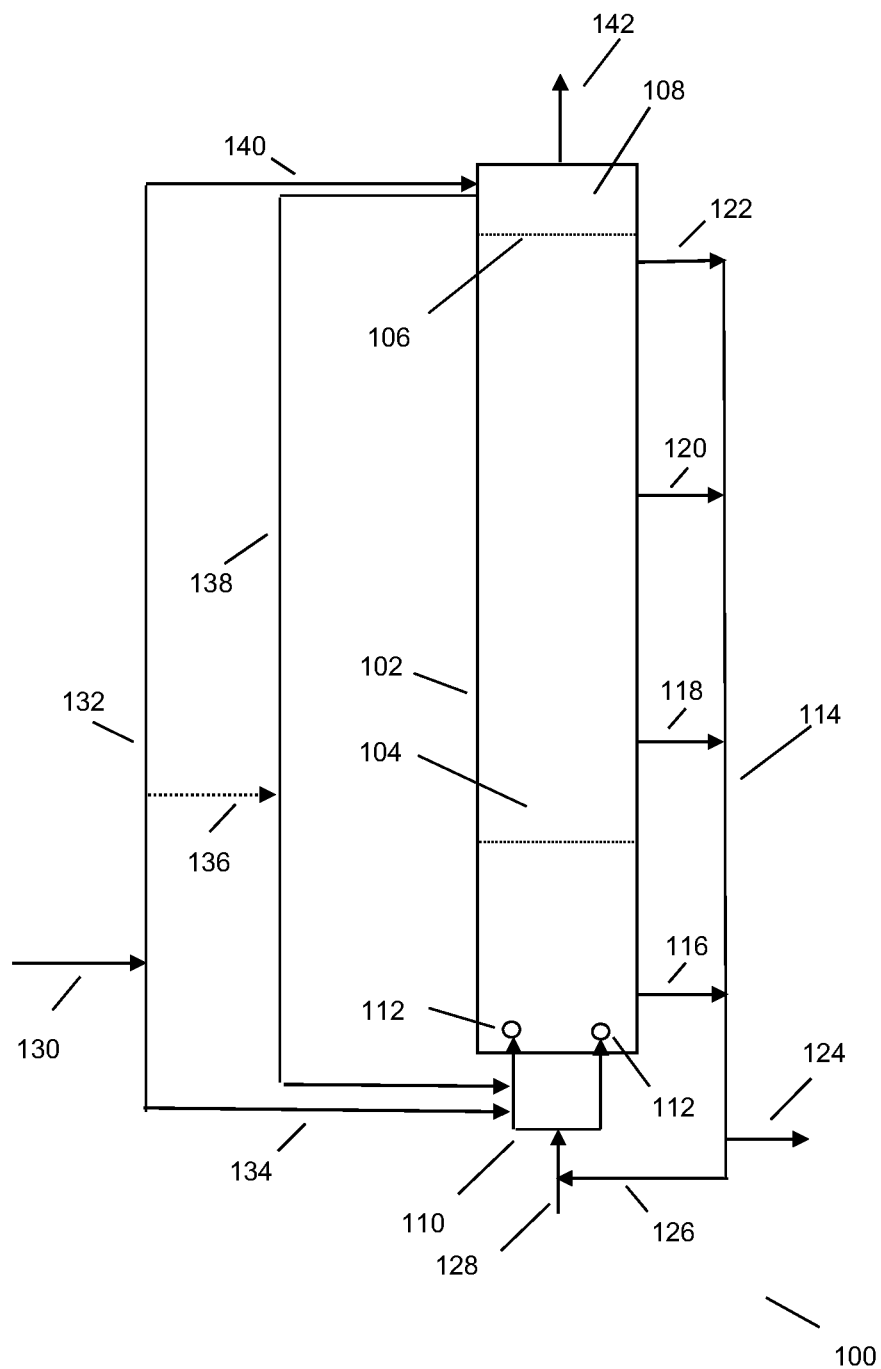
FIG. 1 is a schematic depiction of a deep, bubble column fermentation reactor capable of using the processes of this invention for start-up.

Oxygenated organic compound means one or more organic compounds containing two to six carbon atoms selected from the group of aliphatic carboxylic acids and salts, alkanols and alkoxide salts, and aldehydes. Often oxygenated organic compound is a mixture of organic compounds produced by the microorganisms contained in the aqueous menstruum.

Carbon monoxide inhibition means that microorganisms are adversely affected by a high concentration of dissolved carbon monoxide in the aqueous menstruum resulting in a significantly reduced, e.g., reduced by at least 15 percent, conversion of carbon monoxide or hydrogen per gram of active cells per liter, all other conditions remaining the same. A high concentration of dissolved carbon monoxide means that a higher conversion of carbon monoxide or hydrogen per gram of active cells per liter occurs at a lower dissolved concentration of carbon monoxide. The inhibitory effect may occur in a localized region in the aqueous menstruum; however, the occurrence of a carbon monoxide inhibition is typically observed by assessing the specific activity rate, i.e., the mass bioconsumed per mass of active microorganism per unit time, which under steady-state conditions can be approximated by the overall conversion for the volume of aqueous menstruum in the reactor. The concentration of carbon monoxide dissolved in the aqueous menstruum that results in carbon monoxide inhibition varies depending upon the strain of microorganism and the fermentation conditions.

Aqueous menstruum means a liquid water phase which may contain dissolved compounds including, but not limited to hydrogen, carbon monoxide, and carbon dioxide.

Start-up of a reactor means for purposes herein the operation of commencing bioconsumption of carbon monoxide by microorganisms in the reactor partially filled with aqueous menstruum and continuously or intermittently adding water to increase the volume of aqueous menstruum in the reactor. Start-up continues at least until additional increases in the volume of the aqueous menstruum are no longer sought regardless of microorganism cell density. Preferably, the start-up continues until the oxygenated organic compound is being produced at a rate sufficient for continuous product recovery.

Essential exclusion of oxygen means a molecular oxygen concentration in a gas of less than about 200, preferably less than about 100, parts per million by volume.

Intermittently means from time to time and may be at regular or irregular time intervals.

A concentration of the oxygenated organic compound below that which unduly adversely affects the rate of growth of the culture of microorganisms will depend upon the type of microorganism and the oxygenated organic compound. An unduly adverse effect on the growth rate means that a significant, usually at least a 20 percent, decrease in the growth rate of the microorganisms is observed in comparison to the growth rate observed in an aqueous menstruum having about 10 grams per liter oxygenated organic compound therein, all other parameters being substantially the same.

Uniformity in gas phase dispersion means that the microbubbles of gas at any point in the aqueous menstruum have a mole fraction of carbon monoxide that does not vary by more than 20 percent.

Stable gas-in-liquid dispersion means a mixture of gas bubbles in liquid where the bubbles predominantly flow in the same direction as the liquid, and the dispersion is sufficiently stable that it exists throughout the aqueous menstruum even if bubble sizes change and larger bubbles exist.

Overview

The processes of this invention pertain to starting up deep tank fermentation reactors for anaerobic conversion of gas substrate containing carbon monoxide, hydrogen and carbon dioxide to oxygenated organic compound such as ethanol, acetic acid, propanol, propionic acid, butanol and butyric acid. The processes enable rapid growth of the microorganism culture in the reactor while avoiding carbon monoxide inhibition.

Substrate and Feed Gas

Anaerobic fermentation to produce oxygenated organic compound uses a substrate comprising carbon monoxide, carbon dioxide and hydrogen, the later being for the hydrogen conversion pathway. The gas feed will typically contain nitrogen and methane in addition to carbon monoxide and hydrogen. Syngas is one source of such a gas substrate. Syngas can be made from many carbonaceous feedstocks. These include sources of hydrocarbons such as natural gas, biogas, biomass, especially woody biomass, gas generated by reforming hydrocarbon-containing materials, peat, petroleum coke, coal, waste material such as debris from construction and demolition, municipal solid waste, and landfill gas. Syngas is typically produced by a gasifier. Any of the aforementioned biomass sources are suitable for producing syngas. The syngas produced thereby will typically contain from 10 to 60 mole % CO, from 10 to 25 mole % $CO_2$ and from 10 to 60 mole % $H_2$. The syngas may also contain $N_2$ and $CH_4$ as well as trace components such as $H_2S$ and COS, $NH_3$ and HCN. Other sources of the gas substrate include gases generated during petroleum and petrochemical processing. These gases may have substantially different compositions than typical syngas, and may be essentially pure hydrogen or essentially pure carbon monoxide. The gas substrate may be obtained directly from gasification or from petroleum and petrochemical processing or may be obtained by blending two or more streams. Also, the gas substrate may be treated to remove or alter the composition including, but not limited to, removing components by chemical or physical sorption, membrane separation, and selective reaction. Components may be added to the gas substrate such as nitrogen or adjuvant gases such as ammonia and hydrogen sulfide.

For the sake of ease of reading, the term syngas will be used herein and will be intended to include these other gas substrates.

Deep Tank Fermentation Reactors and Blanketing

The deep tank fermentation reactor can take any form that provides a substantial depth of aqueous menstruum. The deep tank reactor is of a sufficient volume that the fermentation process is commercially viable. Preferably the deep tank reactors are designed to contain at least 1 million, and more preferable at least about 5, say about 5 to 25 million, liters of aqueous menstruum. These reactors are characterized as having a height of at least about 10, often between about 10 and 30, meters and an aspect ratio of height to diameter of at least about 0.5:1, say, 0.5:1 to 5:1, preferably between about 0.75:1 to 3:1. Often commercial-scale reactors are characterized by a width of at least about 5, preferably at least about 7, say, between about 7 and 30, meters. While the reactors are typically circular in cross-section, other cross-sectional configurations can be used provided that uniformity in the liquid phase is obtained. The depth of the aqueous menstruum under steady state production conditions will occupy nearly the full height of the fermentation reactor. The height of the aqueous menstruum will establish a hydrostatic pressure gradient along the axis of the reactor.

The deep tank reactor may be a liquid mixed reactor or preferably a bubble column reactor. Bubble column reactors may contain axial-flow promoting devices such as baffles, down draft tubes and the like although these devices add to the capital costs of the reactors. Hence, most bubble column reactors do not contain these devices.

Liquid mixed reactors use one or more mechanical stirrers. The mechanical stifling should be sufficient to promote the uniformity of liquid composition through the reactor and need not, and preferably is not, used as a generator of a significant fraction of the microbubbles. Usually two or more mechanical stirrers are used at different heights with higher aspect ratio reactors. The design of mechanical stirrers for stirred tank reactors and their positioning within the reactors for very large diameter tanks are well within the skill of a stirred tank reactor designer. Side paddles or side mounted mixers with impellers are frequently used. Axial flow impellers are sometimes used for deep tanks less than about 5 or 7 meters in diameter. Preferably the design of the mechanical stirrers and the positioning within the reactor take into consideration energy costs in generating the liquid flow to obtain uniformity of the aqueous menstruum in the reactor.

By using a motive fluid in an injector to generate the microbubbles for the dispersion, rather than the mechanical stirring, energy savings are realized. Moreover, the injectors can provide better control over the size of the microbubbles. The mechanical stifling is preferably not so robust as to cause undue damage to the microorganisms, yet is still sufficient to achieve the desired uniformity of liquid phase throughout the reactor. A liquid mixed reactor may contain baffles or other static flow directing devices.

As the fermentation is anaerobic, the deep tank fermentation reactor must be sealed and not contain deleterious amounts of oxygen, usually less than 200, preferably less than about 100, parts per million by volume in the blanketing gas or in the gas feed or other source. Accordingly for start-up, the vessel must be filled with a gas not containing reactive oxygen. Although a wide variety of gases for blanketing can be used, such as gases containing carbon dioxide, nitrogen or lower alkane, e.g., alkane of 1 to 3 carbon atoms such as methane and natural gas, cost and availability considerations play a role in the selection of the blanketing gas as well as its acceptability to the anaerobic fermentation process and subsequent unit operations. Thus methane and other normally gaseous hydrocarbons are not preferred. Also, off-gas from one or more anaerobic fermentation reactor or reactors may be used for the initial blanketing especially if the concentration of carbon monoxide in the off-gas is below about 20, preferably below about 15, mole percent.

The processes of this invention, as discussed above, can effectively use these blanketing gases. After start-up has commenced, the composition of the gas in the head space will change as unreacted carbon monoxide and hydrogen and other components contained in the syngas that are not consumed during the initial pass through the aqueous menstruum, will mix with the existing gas in the head space. Preferred initial blanketing gases comprise 0 to about 50, preferably 0 to about 20, mole percent carbon monoxide; 0 to about 70 mole percent carbon dioxide; 0 to about 50, preferably 0 to about 20, mole percent hydrogen; 0 to 100 mole percent nitrogen and 0 to 100 mole percent lower alkane.

The blanketing may be effected in any suitable manner provided that the reactive oxygen is substantially removed.

Oxygenated Compounds and Microorganisms

The start-up of deep tank reactor involves providing a culture of microorganisms, or inoculant, in an aqueous menstruum to the reactor and then growing the culture and increasing the height of the aqueous menstruum to the targeted level for steady state production. The oxygenated organic compounds produced in the processes of this invention will depend upon the microorganism used for the fermentation and the conditions of the fermentation. Bioconversions of CO and $H_2/CO_2$ to acetic acid, n-butanol, butyric acid, ethanol and other products are well known. For example, a concise description of biochemical pathways and energetics of such bioconversions have been summarized by Das, A. and L. G. Ljungdahl, *Electron Transport System in Acetogens* and by Drake, H. L. and K. Kusel, *Diverse Physiologic Potential of Acetogens*, appearing respectively as Chapters 14 and 13 of Biochemistry and Physiology of Anaerobic Bacteria, L. G. Ljungdahl eds., Springer (2003). Any suitable microorganisms that have the ability to convert the syngas components: CO, $H_2$, $CO_2$ individually or in combination with each other or with other components that are typically present in syngas may be utilized. Suitable microorganisms and/or growth conditions may include those disclosed in U.S. patent application Ser. No. 11/441,392, filed May 25, 2006, entitled "Indirect Or Direct Fermentation of Biomass to Fuel Alcohol," which discloses a biologically pure culture of the microorganism *Clostridium carboxidivorans* having all of the identifying characteristics of ATCC no. BAA-624; U.S. Pat. No. 7,704,723 entitled "Isolation and Characterization of Novel Clostridial Species," which discloses a biologically pure culture of the microorganism *Clostridium ragsdalei* having all of the identifying characteristics of ATCC No. BAA-622; both of which are incorporated herein by reference in their entirety. *Clostridium carboxidivorans* may be used, for example, to ferment syngas to ethanol and/or n-butanol. *Clostridium ragsdalei* may be used, for example, to ferment syngas to ethanol.

Suitable microorganisms and growth conditions include the anaerobic bacteria *Butyribacterium methylotrophicum*, having the identifying characteristics of ATCC 33266 which can be adapted to CO and used and this will enable the production of n-butanol as well as butyric acid as taught in the references: "Evidence for Production of n-Butanol from Carbon Monoxide by *Butyribacterium methylotrophicum*," Journal of Fermentation and Bioengineering, vol. 72, 1991, p. 58-60; "Production of butanol and ethanol from synthesis gas via fermentation," FUEL, vol. 70, May 1991, p. 615-619. Other suitable microorganisms include: *Clostridium Ljungdahlii*, with strains having the identifying characteristics of ATCC 49587 (U.S. Pat. No. 5,173,429) and ATCC 55988 and 55989 (U.S. Pat. No. 6,136,577) that will enable the production of ethanol as well as acetic acid; *Clostridium autoethanogenum* sp. nov., an anaerobic bacterium that produces ethanol from carbon monoxide. Jamal Abrini, Henry Naveau, Edomond-Jacques Nyns, Arch Microbiol., 1994, 345-351; Archives of Microbiology 1994, 161: 345-351; and *Clostridium Coskatii* having the identifying characteristics of ATCC No. PTA-10522 filed as U.S. Ser. No. 12/272,320 on Mar. 19, 2010. All of these references are incorporated herein in their entirety.

Aqueous Menstruum And Fermentation Conditions

The aqueous menstruum will comprise an aqueous suspension of microorganisms and various media supplements. Suitable microorganisms generally live and grow under anaerobic conditions, meaning that dissolved oxygen is essentially absent from the fermentation liquid. The various adjuvants to the aqueous menstruum may comprise buffering agents, trace metals, vitamins, salts etc. Adjustments in the menstruum may induce different conditions at different times such as growth and non-growth conditions which will affect the productivity of the microorganisms. Previously referenced U.S. Pat. No. 7,704,723 discloses the conditions and contents of suitable aqueous menstruum for bioconversion CO and $H_2/CO_2$ using anaerobic microorganisms.

The top of the deep, bubble column fermentation zones may be under pressure, at atmospheric pressure, or below ambient pressure. The menstruum is maintained under anaerobic fermentation conditions including a suitable temperature, say, between 25° and 60° C., frequently in the range of about 30° to 40° C. The conditions of fermentation, including the density of microorganisms, aqueous menstruum composition, and fermentation zone depth, are preferably sufficient to achieve the sought conversion efficiency of hydrogen and carbon monoxide.

The average residence time of the gas in the fermentation zone (average time for the bubble to move from the point of introduction to the upper surface of the menstruum) will depend upon not only the depth of the aqueous menstruum but also the size of the bubble when introduced and the internal fluid flows in the reactor. Thus the residence time will change as the height of the aqueous menstruum is increased during the start-up.

Initiating Start-Up:

For start-up, the vessel is initially charged with an aqueous menstruum containing a combination of microorganisms and nutrients up to a height of about 10 meters, preferably between about 1.5 and 5 or 7 meters. By maintaining a low level of aqueous menstruum and low head pressure, the rate of transfer of carbon monoxide from the gas phase to the liquid phase can be readily modulated thereby reducing the risk of carbon monoxide inhibition. Another advantage provided by using the low level of aqueous menstruum at the initiation of start-up is that the ratio of motive liquid flow rate to aqueous menstruum volume can be higher and thereby enhance mixing of the aqueous menstruum and providing more uniform distribution of the gas phase in the aqueous menstruum, especially for deep, bubble column reactors. Particularly when more than one injector is used, an injector may be used solely for the purpose of providing mixing, i.e., only motive liquid is introduced by the injector.

The initial aqueous menstruum typically comprises an inoculation amount of aqueous menstruum from a seed farm or lyophilized or otherwise dormant microorganism with the balance being an aqueous charge containing nutrients and other adjuvants for the fermentation. The initial density of the microorganisms in the initial charge is between about 0.03 and 3, often between about 0.05 and 1, grams per liter.

The initial concentration of dissolved carbon monoxide in the aqueous menstruum should be sufficient to enable the microorganisms to be nourished, but preferably below saturation under the conditions of the fermentation, e.g., in the range of 0.01 to 0.1 millimole of dissolved carbon monoxide per liter of aqueous menstruum.

The substrate gas feed may commence before, simultaneously with and shortly after the initial aqueous menstruum has been inoculated with the culture of microorganisms. Carbon monoxide in the gas substrate should be supplied at a rate and under conditions that the rate of mass transfer into the aqueous menstruum approximates the rate that the culture of microorganisms in the aqueous menstruum converts carbon monoxide, thereby maintaining the dissolved carbon monoxide concentration below levels that are inhibitory. A number of factors affect the rate of mass transfer, including, but not limited to, the mole fraction of carbon monoxide in the gas phase, the concentration of carbon monoxide in the adjacent liquid phase, the gas bubble size, and hydrostatic pressure.

The balance between providing sufficient gas substrate for robust microorganism growth and carbon monoxide inhibition during the start-up operation can be monitored in any convenient manner. For instance, the supply of gas feed, concentration of carbon monoxide in the gas feed, and microbubble size can be established based upon maintaining a constant concentration of carbon monoxide in the aqueous menstruum. Other parameters that can be monitored and used to adjust these variables include net carbon monoxide and hydrogen consumption, net carbon dioxide production, microorganism density and rate of production of oxygenated organic compound. Similarly, the supply of gas feed, concentration of carbon monoxide in the gas feed, and microbubble size can be adjusted to provide a mass transfer rate of carbon monoxide to the aqueous menstruum matching the consumption rate of carbon monoxide by the microorganism culture in the aqueous menstruum. Thus, as the culture grows, modulation occurs to increase the mass transfer to meet the needs of the culture. The size of the culture can be derived by determining the live cell density or through approximation from the optical density of the menstruum.

Gas Feed Injection

The processes of this invention use at least one injector using a motive fluid for supplying gas feed to the aqueous menstruum. Gas feed includes fresh syngas or other substrate gas as well as recycled gas from the head space and any other gas fed to the reactor for any purpose, including but not limited to gaseous adjuvants and diluents. Preferably the reactor contains 2 or more injectors, and commercial scale reactors will often contain at least 2, often 4 to 8 or 10, laterals of injectors with as many as 100 or more injectors. The number of injectors used is typically selected based upon the ability to be able to transfer adequate amounts of gas substrate under steady-state operating conditions and to enhance cross-sectional uniformity of the gas phase in the reactor. As the amount of gas substrate needed by the culture during start-up is less than that required at full capacity commercial operation, flexibility in the use of injectors is provided for start-up operations. For instance, gas feed may be supplied to the aqueous menstruum during start-up by only one or a few injectors with the remaining injectors either being turned off or being used to recycle liquid in the vessel to enhance mixing and uniformity throughout the aqueous menstruum. More injectors would be used to supply gas feed as the start-up progresses to meet the nourishment needs of the culture. For the purposes herein, this is referred to as injector sequencing.

The injectors may be jet mixers/aerators or slot injectors. Slot injectors are preferred, one form of which is disclosed in U.S. Pat. No. 4,162,970. These injectors operate using a motive liquid. The injectors, especially slot injectors, are capable of operating over a wide range of liquid and gas flow rates and thus are capable of significant turn down in gas transfer capability. The injectors are characterized as having nozzles of at least about 1, often about 1.5 to 5, say, 2 to 4, centimeters as the cross-sectional dimension in the case of jet injectors or as the smaller cross-sectional dimension in the case of slot injectors. The large cross-sectional dimension of the injectors provides several benefits in addition to being able to produce microbubbles. First, they are not prone to fouling including where aqueous menstruum is used as the motive liquid as would be a sparger designed to produce microbubbles. Second, where the aqueous menstruum is used as the motive fluid, high momentum impact of the microorganisms with solid surfaces is minimized thereby minimizing the risk of damage to the microorganisms. Third, the energy required to provide microbubbles of a given size is often less than that required to form microbubbles of that size using a microbubble sparger. Fourth, a high turn down ratio can be achieved. And fifth, the microbubble size can be easily varied over a wide range.

The bubble size generated by the injectors will be influenced by, among other factors, the rate of liquid flow through the injector and the ratio of gas phase to liquid phase passing through the injector as well as characteristics of the aqueous menstruum itself including, but not limited to its static liquid depth. Consequently, an injector can be operated to provide a selected bubble size which enhances the ability to use the injector in a modulation mode, i.e., provide the adjustment in the rate of transfer of carbon monoxide to the liquid phase based upon the size of the culture and its ability to bioconvert the carbon monoxide. The modulation can also be used to obtain, if desired, a stable gas-in liquid dispersion. The modulation can be obtained by changing one or more of (i) the gas to liquid flow ratio to the injector thus changing the volume of gas feed and (ii) changing the rate of motive liquid and thus the bubble size which affects the rate of transfer of carbon monoxide from the gas phase to liquid phase. Additionally, modulation can be obtained by changing the gas feed composition and thus the mole fraction of carbon monoxide in the gas feed.

At the commencement of start-up it may be desired to use larger bubble sizes, preferably in the range of 100 to 5000 microns in diameter to achieve the initial modulation and avoid carbon monoxide inhibition. Depending upon the ability of the specific injector design to produce such large bubbles of gas feed, the gas feed or a portion of the gas feed may be introduced by sparging. A portion of the gas feed may be introduced as even larger bubbles where enhanced mixing of the aqueous menstruum is sought. The sparger may be phased out as the size of the culture increases and the smaller bubble sizes produced by the injectors can be used while avoiding carbon monoxide inhibition yet achieve advantageous culture growth rates.

Except as stated in the previous paragraph, the gas feed during start-up is introduced as microbubbles having a diameter of less than about 0.5, millimeters. Most preferably the gas substrate is introduced by the injector into the menstruum in the form of microbubbles having diameters in the range of 0.01 to 0.5, preferably 0.02 to 0.3 millimeter. The gas substrate may be introduced into the bottom portion of the deep, tank reactor as a gas stream or as a gas in liquid dispersion as disclosed in U.S. patent application Ser. No. 12/826,991, filed Jun. 30, 2010. The presence of the oxygenated organic compound and/or other surface active agent enhances the formation of fine microbubbles.

The motive liquid may be any suitable liquid for introduction into the fermentation reactor. Hence, the liquid is preferably suitable for use as the aqueous menstruum. At the initial start-up, one or more of the inoculant and the additional aqueous menstruum to make the initial liquid level of the aqueous menstruum can be used as motive liquids. Advantageously, the motive liquid is one or more of aqueous menstruum, liquid derived from aqueous menstruum or make-up liquid to replace aqueous menstruum withdrawn from product recovery.

The flow rate of motive liquid used in an injector will depend upon the type, size and configuration of the injector and the sought bubble size of the gas feed. In general, the rate is preferably sufficient to provide a velocity of the dispersion stream leaving the injector of about 0.05 to 5, say, 0.1 to 2, meters per second. Typically the ratio of gas to motive liquid is in the range of from about 0.1:1 to 3:1, say, 0.5:1 to 2:1, actual cubic meters per cubic meter of motive liquid. As the start-up approaches steady-state operating conditions, the flow rate of the motive liquid typically increases as does the ratio of gas to motive fluid. At steady-state conditions, the velocity of the dispersion stream leaving the injector is frequently in the range of 0.5 to 5 meters per second and the ratio of gas to motive liquid is in the range of from about 1:1 to 3:1 actual cubic meters per cubic meter of motive liquid.

Often the microbubbles form a stable gas-in-water dispersion. The introduction of the microbubbles into the aqueous menstruum places the microbubbles in a dynamic environment. The height of the aqueous menstruum means that microbubbles in the dispersion will experience different static pressure heads as they travel upwardly through the reactor. Increased pressure will, all else substantially the same, reduce the size of a microbubble and thus also increase its surface area to volume ratio. For a given gas feed rate, a greater surface area will be provided by the smaller microbubbles which enhances mass transfer. The size of a microbubble will also be affected by the diffusion of gases from the microbubble to the liquid phase. As carbon monoxide and hydrogen constitute a significant mole fraction of the microbubble as it is introduced into the aqueous menstruum, the dynamic conditions will promote a population of microbubbles that have small diameters to aid in maintaining the gas-in-water dispersion throughout the reactor.

The injectors may be located at one or more locations in the reactor and oriented in any suitable direction. Injectors are typically located in a lower portion of a deep, bubble column or deep, liquid mixed reactor. By locating the injectors over the height of the reactor, the uniformity of composition of the gas-in-liquid dispersion in the aqueous menstruum is promoted and less mechanical stifling energy may be required to maintain the sought uniformity. However, injectors used for start-up are usually those contained within the aqueous menstruum. Liquid mixed reactors typically provide defined liquid currents past the injectors. Often the injectors are oriented to promote admixing of the gas feed with the aqueous menstruum and distribution in the reactor.

Use of Off-Gas Recycle

As stated above, the head space above the aqueous menstruum is initially blanketed to exclude reactive oxygen. As the start-up progresses, the composition of the gas above the aqueous menstruum will change due to one or more of consumption of carbon monoxide, the build-up of unreacted substrate, and purge due to addition of new substrate and/or dilution gas. The gas in the fermentation reactor above the aqueous menstruum is referred to herein as the off-gas.

Preferably at least a portion of the off-gas is recycled to the aqueous menstruum during initial start-up. Where the off-gas contains carbon monoxide and hydrogen, it can serve as the gas feed until the mass transfer of carbon monoxide and hydrogen to the aqueous menstruum is not sufficient to maintain the sought growth of the culture. It can also be admixed with fresh syngas to provide a combined gas feed. Where the blanketing gas is rich in nitrogen or carbon dioxide, the gas feed will likely require fresh syngas to provide the sought mass of carbon monoxide and hydrogen to nourish the culture. The recycled off-gas may be admixed with fresh syngas or may be injected separately from the fresh syngas, in which case, the concentration of carbon monoxide in the aqueous menstruum can be modulated by reducing the net mole fraction of carbon monoxide in the system.

The off-gas, even where initially only nitrogen or carbon dioxide, will quickly start to accumulate gas substrates as the start-up progresses and unreacted carbon monoxide and hydrogen enter the headspace. By regulating the amount of feed gas and recycled off-gas or other diluent gas it is possible to control the mole fraction of carbon monoxide in the headspace to the desired level. Frequently, the concentration of carbon monoxide in the head space during start-up is maintained at less than about 20, preferably less than about 15, say, between about 5 and 15, mole percent. In a preferred process in accordance with this invention, recycling off-gas is used to modulate the carbon monoxide supply rate to the aqueous menstruum. The recycled off-gas may be the gas feed to one or more injectors, or it may be admixed with fresh syngas to provide a composite gas feed for one or more injectors. Where the off-gas contains significant concentrations of carbon monoxide, at least one of carbon dioxide, nitrogen or alkane can be admixed with the recycle gas to provide a gas feed having a desired carbon monoxide concentration for supply to the aqueous menstruum. When the culture has grown to a mass requiring more substrate than can be provided by the off-gas, fresh syngas feed can be commenced. Either an injector using recycled off-gas or an injector using fresh syngas can modulate by changing gas flow rate.

Progressing the Start-Up

The start-up of the deep, bubble column fermentation needs to accomplish both a robust growth of the culture of microorganisms and eventually increasing the height of the aqueous menstruum. Both have an effect on the rate of gas feed and on the risk of overdosing the microorganisms with carbon monoxide. With respect to the latter, as the height of the aqueous menstruum increases, the saturation concentration of carbon monoxide where introduced into the aqueous menstruum increases assuming the mole fraction of carbon monoxide in the gas is maintained constant. The higher partial pressure increases the driving force for transfer of carbon monoxide from the gas phase to the aqueous menstruum and the concomitant risk of carbon monoxide oversupply.

A preferred start-up operation is initially to focus on increasing the density of the microorganisms before significantly increasing the volume of aqueous menstruum. Often, the cell concentration in the initial charge of aqueous menstruum is increased to at least about 0.5, say, about 0.5 to 1.5, grams per liter before increasing the volume of the aqueous menstruum. The volume increase may be continuous or intermittent. In either event, the cell density should be maintained at or above 0.5 grams per liter. At least initially, the growth of the culture can be effected without withdrawing liquid for product recovery. However, when the concentration of oxygenated organic compound builds up to a predetermined level, such as where the growth of the culture may be adversely affected or where sufficient concentration exists for product recovery, a stream can be taken to product recovery or disposal and additional aqueous menstruum including nutrients provided to the vessel. Also a purge may be taken to remove solids and maintain a predetermined average mean cell retention time.

In an aspect of this invention, the start-up operation is operated in substantially a liquid retention mode, i.e., substantially no product or purge is taken to remove solids and no predetermined average mean cell retention time is maintained. The addition of aqueous menstruum during start-up can be intermittent or continuous and is usually at a rate sufficient to maintain the concentration of oxygenated organic compound below that which adversely affects the growth of the microorganisms (product inhibition). The concentration where product inhibition occurs will depend upon the strain of microorganism used, the fermentation conditions and the nature of the oxygenated organic compound. Often, start-up can be accomplished and cell densities of between about 1 to 10 grams per liter can be achieved without sufficient build-up of oxygenated organic compound that the growth rate of the culture of microorganisms is adversely affected. The advantages of this aspect of the invention include not only avoiding a loss of microorganisms by withdrawing a liquid stream from the reactor but also retaining nutrients, including those provided by dead cells, in the aqueous menstruum.

Progressing start-up to steady-state operation as quickly as feasible is desired. A number of factors relate to the robustness of the growth of the microorganisms. These factors include the fermentation conditions, including the presence of nutrients and adjuvants, as well as transferring carbon monoxide and hydrogen to the liquid phase of the aqueous menstruum at a rate matching the ability of the microorganisms to bioconvert the substrate to oxygenated product. The processes of this invention that modulate the supply of carbon monoxide, enable the operator to fine tune the mass transfer of carbon monoxide to the liquid phase and avoid a build-up of dissolved carbon monoxide that could cause carbon monoxide inhibition.

DRAWINGS

A general understanding of the invention and its application may be facilitated by reference to the Figures.

FIG. 1 is a schematic depiction of an apparatus generally designated as 100 suitable for practicing the processes of this invention. FIG. 1 omits minor equipment such as pumps, compressors, valves, instruments and other devices the placement of which and operation thereof are well known to those practiced in chemical engineering. FIG. 1 also omits ancillary unit operations. The process and operation of FIG. 1 will be described in the context of the recovery and production of ethanol. The process is readily adaptable to starting up anaerobic fermentation reactors to make other oxygenated products such as acetic acid, butanol, propanol and acetone.

Apparatus 100 contains deep, bubble column fermentation reactor 102 adapted to hold aqueous menstruum. The height of the initial charge of aqueous menstruum for start-up is designated by line 104 and the targeted height for steady-state operation is designated by line 106. The region above the aqueous menstruum is head space 108. As can be readily appreciated, head space 108 will change in volume during the start-up process. At the bottom of fermentation reactor 102 are a plurality of injector laterals 112, only two of which are shown, with each injector lateral being in fluid communication with flow distribution network 110. Each injector lateral 112 contains a plurality of slot injectors. As depicted, flow distribution network 110 is adapted to provide separately each of recycled off-gas, fresh syngas and motive liquid to each injector lateral 112, and each injector lateral 112 may be operated with different gas compositions, liquid flow rates and gas/liquid ratios. While more complex, each injector lateral 112 can be designed to provide a nozzle, or groups of nozzles, on the lateral with different gas compositions, liquid flow rates and gas/liquid ratios.

Apparatus 100 is provided with liquid recycle header 114 adapted to withdraw aqueous menstruum from vessel 102 at various heights. Four withdrawal lines are shown, although more or fewer can be used. Line 116 is sufficiently low that it can withdraw liquid aqueous menstruum from the initial charge. Lines 118 and 120 are positioned at different heights in the midsection of vessel 102, and line 122 is position in an upper portion of vessel 102 for withdrawal of aqueous menstruum at its steady-state operation height. In general, it is preferred to withdraw aqueous menstruum at an upper portion of the menstruum where the concentration of carbon monoxide and hydrogen in the liquid phase is lower. Alternatively, aqueous menstruum can be withdrawn from line 116 and by backpressure adjust the height of the aqueous menstruum in reactor 104.

Line 124 is in fluid communication with header 114 and is adapted to withdraw a portion or all of the aqueous menstruum for purge and product recovery. Preferably during start-up substantially no liquid is withdrawn via line 124. Line 126 is adapted to pass fermentation liquid to flow distribution network 110 for use as a motive liquid in injector laterals 112. Make up liquid, which may include nutrients and other adjuvants, for the aqueous menstruum is provided by line 128 and is shown as being admixed with the recycled aqueous menstruum prior to passing to flow distribution network 110 although it could be directed to a separate pipe in flow distribution network 110 for delivery to injector laterals 112.

Syngas to provide gas substrate is provided to apparatus 100 via line 130 to syngas header 132. Syngas header 132 is provided with line 134 to provide syngas to flow distribution network 110. It can also provide syngas via line 136 to recycle header 138 and to head space 108 via line 140. Recycle off-gas is passed from the top of vessel 102 via recycle header 138 to flow distribution network 110. Line 142 in fluid communication with the top of vessel 102 removes off-gas from assembly 100 for processing or disposal.

In operation the syngas provided by line 134 to flow distribution network 110 can be admixed with recycle off-gas provided by recycle header 138 and provided to an injector lateral to provide a mixed gas feed, or the fresh syngas can be separately directed by flow distribution network 110 to each injector lateral 112 so that the gas feed from an injector lateral may be 100 percent recycled off-gas and 100 percent syngas from another injector lateral. Line 136 provides syngas to recycle header 138 where the fresh syngas and recycled off-gas are admixed and directed to flow distribution network 110. In this embodiment the gas feed to an injector lateral would be an admixed gas. Another alternative is to direct fresh syngas to head space 108 via line 140 to provide a syngas and off-gas admixture for recycle via line 138 to flow distribution network 110.

Figure 2:
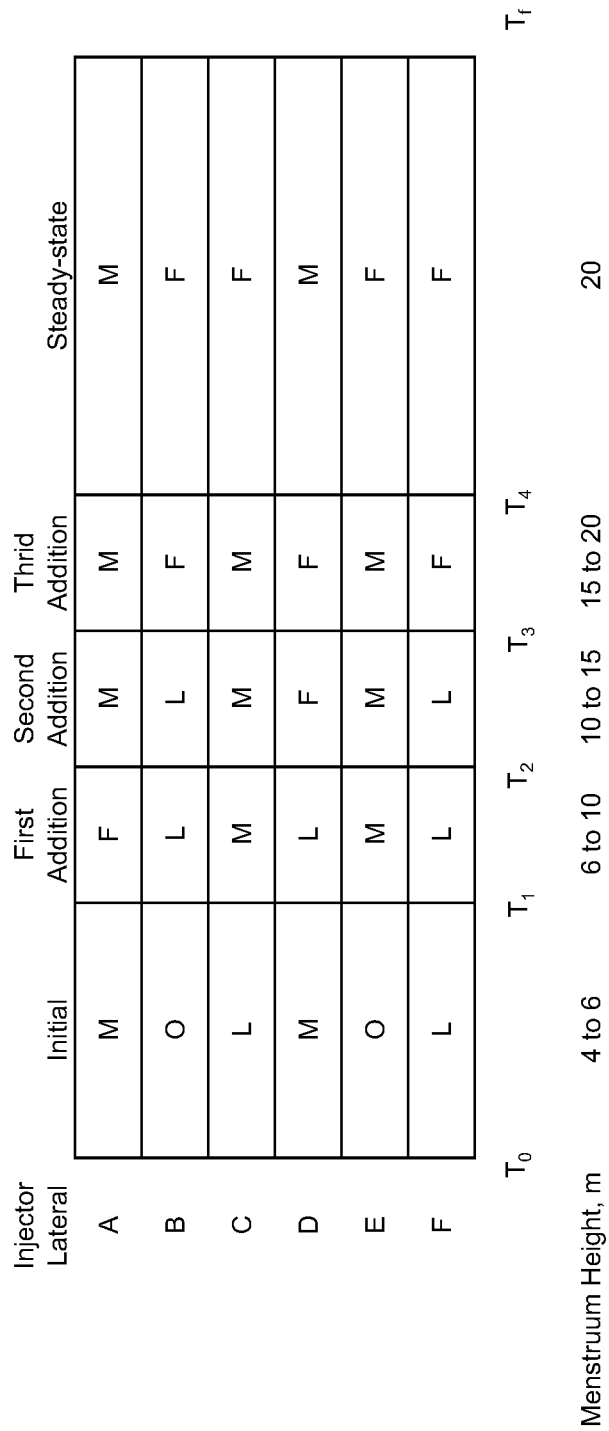
FIG. 2 is a representative sequencing chart for one type of start up using the processes of this invention.

FIG. 2 provides a chart setting forth a representative sequencing of injectors for a start-up in accordance with the processes of this invention. It is to be understood that other sequencing can be accomplished while still obtaining the benefits of this invention and are encompassed by this invention.

For the sake of illustration the apparatus of FIG. 1 has six injector laterals 112 (laterals A, B, C, D, E and F) positioned equidistant from each other at the base of vessel 102. Each of the laterals contains a plurality of slot injectors. The targeted height of the aqueous menstruum in deep, bubble column fermentation vessel 102 is 20 meters.

Initial Charge and First Growth Stage Operation:

Vessel 102 which has been blanketed with a mixture of syngas and nitrogen is filled to a height of 3 to 6 meters with aqueous menstruum obtained from a seed farm and additional aqueous medium containing nutrients to provide an aqueous menstruum having a live cell density of about 0.03 to 3 grams per liter. The head space gas contains the desired mole fractions of carbon monoxide and hydrogen for the gas feed to the aqueous menstruum. During the initial stages the headspace gas is recycled via the slot injectors via a venturi action. It is important to match the rate of gas transfer with the carbon monoxide uptake capacity of the microorganisms at this stage while simultaneously providing sufficient mixing. This is accomplished by the following. A set number of nozzles are dedicated to providing gas transfer while others are used to either recirculate liquid only or recycle gas as large bubbles to help achieve the desired mixing intensity.

During start-up the fermenter can be operated in a liquid retention mode where essential nutrients, trace metals and vitamins are supplied to allow maximum growth and minimal increase in the liquid volume, or the liquid volume can be gradually increased by addition of additional aqueous menstruum beyond a concentrated nutrient solution.

In either situation the need for gas substrate transfer to the aqueous menstruum will increase as the culture of microorganisms grows and the achievable carbon monoxide uptake rate increases. At this stage of the start-up process, fresh syngas may be fed direct to the headspace or blended with the gas being recycled. The amount of syngas fed can be controlled as a feedback loop based on the carbon monoxide mole fraction in the headspace.

The gas transfer can be increased to meet the continually increasing uptake capability of the culture of microorganisms by either or both of placing more laterals in gas transfer mode or increasing the liquid flow through the nozzles to increase the transfer rate by producing smaller bubbles. The nozzles can be operated in a modulating mode (designated by "M" on the chart of FIG. 2) which means that the ratio of gas feed to motive liquid and/or the motive liquid flow rate are adjusted to increase or decrease the rate of mass transfer of carbon monoxide and hydrogen to the aqueous menstruum through adjusting microbubble size and gas flow rate. The nozzles can be operated in a fixed mode (designated by "F" on the chart of FIG. 2) which means that the nozzle is generating the sought microbubble size targeted to provide the sought mass transfer of carbon monoxide and hydrogen to achieve the targeted conversion efficiency once the reactor has been started-up and is in steady-state operation. Other nozzles (designated by "O" on the chart of FIG. 2) are not yet in operation to supply liquid or gas to vessel 102.

In further detail and with reference to the chart, the vessel is initially filled to a height where aqueous menstruum can be withdrawn from vessel 102 via line 116. A recycle flow of aqueous menstruum is used as the motive liquid for the nozzles. Recycle off-gas from line 138 is passed to some of the laterals at time $T_0$ as described above. The nozzles are generally operated in a modulating mode. It is also feasible to operate one or more of the laterals in a fixed mode while operating one or more of the remaining nozzles in a modulating mode. Similarly, one or more laterals may be fed only recycled aqueous menstruum (designated by L on the chart) to promote mixing of the aqueous menstruum.

First Liquid Addition Stage and Second Growth Stage:

At time $T_1$ the liquid volume is built up in the reactor to a height where it is possible to provide the motive liquid via line 118 so that line 116 can be taken out of service if desired. If desired, line 116 can remain in service with, or without, operation of any of lines 118, 120, and 122. Eventually as additional aqueous medium is added to increase the height of the aqueous menstruum recycle of off-gas via the venturi action becomes impossible. At this point the gas transfer rate can be controlled by modulating the rate of syngas addition and liquid recycle flow to achieve the gas transfer rate that does not exceed the biological uptake capacity. Different injector laterals can be operated under different conditions to achieve the desired transfer rate. If desired, at least a portion of the off-gas can be recycled by using a blower.

Second Liquid Addition Stage and Third Growth Stage:

At time $T_2$ the liquid volume is built up in the reactor to a height where it is possible to provide the motive liquid via line 120 and line 118 can be taken out of service if desired. As the composition of the off-gas is changing due to consumption of carbon monoxide and hydrogen, a switch from recycled off-gas to syngas maintains the sought supply of gas substrate. Some off-gas recycle may still be used to control the net mole fraction of carbon monoxide as needed or desired.

Third Liquid Addition Stage and Steady-State Operation:

At time $T_3$ the liquid volume is built up in the reactor to a height where it is possible to provide the motive liquid via line 122 and line 120 can be taken out of service if desired. At time $T_4$ the cell density of the aqueous menstruum has reached the sought density and operating height and steady-state operations commence There are many alternatives to the sequence of the chart. For instance, more nozzles can be used in the modulating mode at start-up to provide larger bubbles to slow carbon monoxide transfer to the aqueous menstruum. After the initial growth stage, additional aqueous media can be continuously or periodically added to maintain a relatively constant cell density. Where the blanketing gas has a lower concentration of carbon monoxide than the syngas or has no carbon monoxide, it may be admixed with syngas to provide a gas feed to the nozzles. Similarly, where the head space initially contains syngas, recycled gas may be admixed with carbon dioxide, methane, natural gas, nitrogen or other substantially inert gas to reduce the carbon monoxide concentration in the gas feed to the aqueous menstruum.

Figure 3:
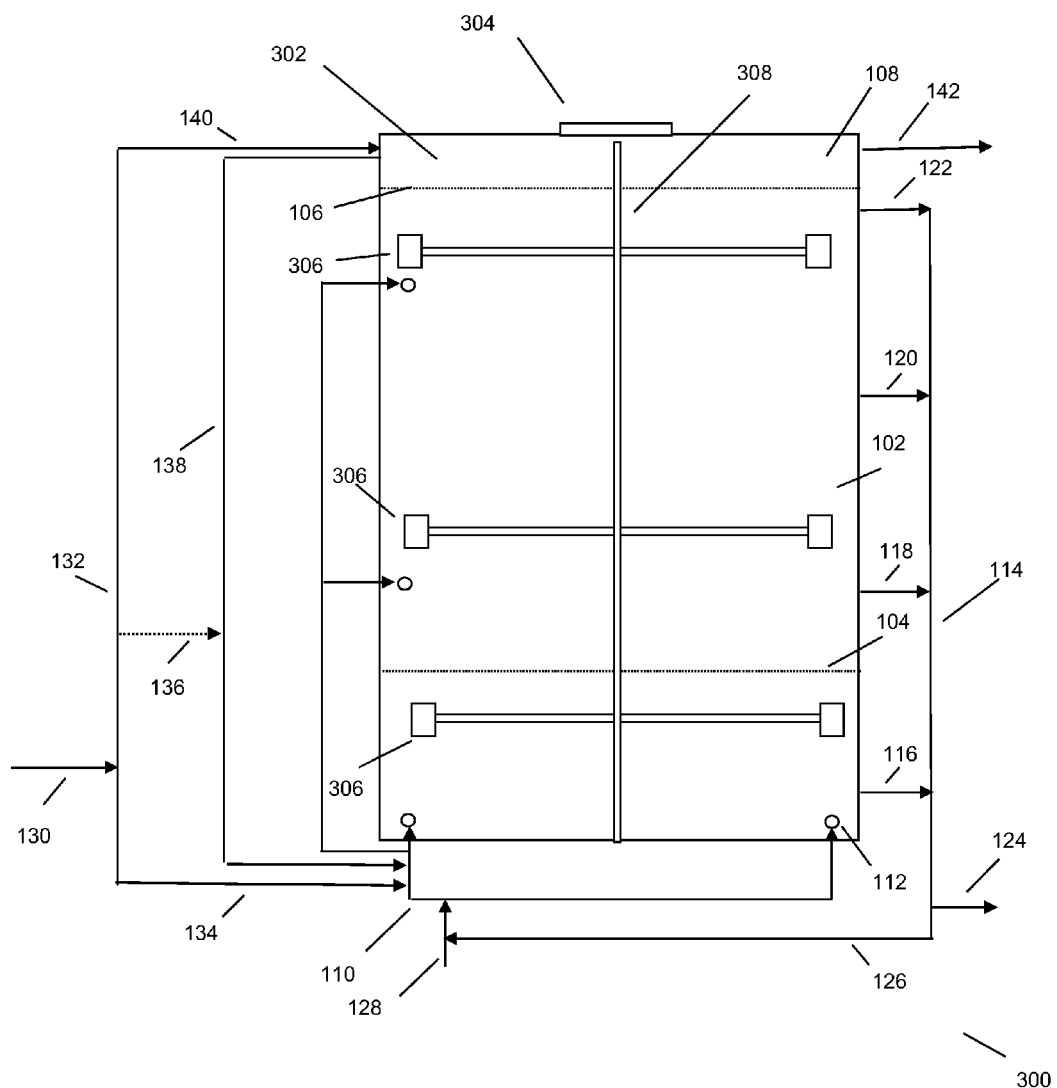
FIG. 3 is a schematic depiction of a deep, liquid mixed reactor capable of using the processes of this invention for start-up.

FIG. 3 is a schematic representation of apparatus 300 which is a deep, liquid mixed reactor. FIG. 3 omits minor equipment such as pumps, compressors, valves, instruments and other devices the placement of which and operation thereof are well known to those practiced in chemical engineering. FIG. 3 also omits ancillary unit operations. The process and operation of FIG. 3 will be described in the context of the recovery and production of ethanol. The process is readily adaptable to starting up anaerobic fermentation reactors to make other oxygenated products such as acetic acid, butanol, propanol and acetone.

Parts of apparatus 300 that are similar to those of apparatus 100 of FIG. 1 are identified by the same identification numbers, and reference should be made to the discussion of FIG. 1 for the description of the parts.

Apparatus 300 is equipped with agitator 302. Agitator 302 is shown as having three paddle blades 306 on a center axle 308; however, fewer or more blades can be used. Motor 304 powers agitator 302 and controls the revolutions per minute. Apparatus 300 also differs from apparatus 100 in that injector laterals 112 are provided at different elevations in vessel 102. In steady-state operation, apparatus 300 recycles a portion of the off-gas to achieve targeted conversion efficiencies. This recycle, in combination with the agitation of the aqueous menstruum, enables the gas feed to be introduced over the height of the aqueous menstruum without undue adverse effects on conversion efficiency. This supply of feed gas at multiple heights further attenuates the risk of carbon monoxide inhibition since not all the gas feed is being introduced where high static head pressures, and thus high carbon monoxide partial pressures that increase the rate of mass transfer, exist. If desired, at least a portion of the start-up of apparatus 300 can be readily achieved without the need for agitation using the modulation achievable with the injectors.

It is claimed:

1. A process for starting-up a commercial scale, deep tank reactor for the anaerobic bioconversion of a gas substrate derived from the gasification of carbonaceous materials, the reforming of natural gas, or biogas from anaerobic digestion or comprising industrial off-gas streams and that comprises carbon monoxide, hydrogen and carbon dioxide in an aqueous menstruum containing microorganisms suitable for converting said substrate to oxygenated organic compound wherein the start-up is initiated with the menstruum containing microorganisms at an initial lower liquid height and the height of the menstruum containing microorganism is increased continuously or intermittently and the reactor has a volume of at least 25 million liters, the process comprising:
    (a) blanketing said reactor above the aqueous menstruum in a head space with at least one of carbon dioxide, nitrogen, and lower alkane to the essential exclusion of oxygen;
    (b) initially providing aqueous menstruum and microorganisms in the reactor to a depth less than about 10 meters, said aqueous menstruum being under fermentation conditions and having a concentration of said microorganisms of between about 0.03 and 3 gram per liter;
    (c) continuously supplying gas feed to a bottom portion of the reactor at a rate sufficient to increase the concentration of microorganisms, said gas feed comprising said gas substrate being supplied to a bottom portion of said reactor via at least one injector using a motive liquid to form microbubbles having a diameter of less than about 500 microns; and (d) increasing intermittently or continuously the volume of aqueous menstruum in said reactor to the desired capacity while increasing the concentration of microorganisms to between 3 and 500 times that in step (b), wherein by at least one of: (i) adjusting the gas to liquid flow ratio through an injector, (ii) changing the rate of liquid flow through an injector, and (iii) adjusting the carbon monoxide mole fraction in the gas feed by admixture with at least one other gas, the mass transfer of carbon monoxide to the aqueous menstruum in the reactor is modulated to obtain the growth of step (c) but is maintained below that amount which results in carbon monoxide inhibition.

2. The process of claim 1 wherein the blanketing gas of step (a) contains carbon monoxide and the gas feed of step (c) comprises the blanketing gas during at least a portion of the start-up process.

3. The process of claim 2 wherein syngas is provided to the head space.

4. The process of claim 1 wherein the reactor is a bubble column reactor.

5. The process of claim 1 wherein the reactor is a liquid mixed reactor.

6. The process of claim 1 wherein the concentration of the microorganisms is increased to between about 1 and 10 grams per liter.

7. The process of claim 1 wherein the injectors comprise slot injectors.

8. The process of claim 1 wherein the motive liquid comprises aqueous menstruum from the reactor.

9. The process of claim 1 wherein at least a portion of the gas in the head space is recycled as a portion of the gas feed supplied by step (c).

10. The process of claim 9 wherein the recycled gas is admixed with fresh syngas prior to supply to the aqueous menstruum.

11. The process of claim 1 wherein two or more injectors are used and during at least a portion of the start-up process, the injectors are sequenced.

12. The process of claim 11 wherein for an initial portion of the start-up process an injector is operated using only motive liquid and for a later portion of the start-up process, said injector is operated using gas feed and motive liquid.

13. The process of claim 1 wherein during an initial portion of the start-up process an injector is operated as a venturi injector.

14. The process of claim 1 wherein for at least a portion of the start-up process, the reactor is operated in substantially liquid retention mode.

15. The process of claim 1 wherein at the initiation of the start-up, the gas feed is supplied as bubbles in the range of 100 to 5000 microns in diameter.

16. A process for starting-up a commercial scale deep tank reactor for the anaerobic bioconversion of a gas substrate derived from the gasification of carbonaceous materials, the reforming of natural gas, or biogas from anaerobic digestion or comprising industrial off-gas streams and that comprises carbon monoxide, hydrogen and carbon dioxide in an aqueous menstruum containing microorganisms suitable for converting said substrate to oxygenated organic compound wherein the start-up is initiated with the menstruum containing microorganisms at an initial lower liquid height and the height of the menstruum containing microorganism is increased continuously or intermittently and the reactor has a volume of at least 25 million liters, the process comprising: (a) blanketing said reactor above the aqueous menstruum in a head space with at least one of carbon dioxide, nitrogen, and lower alkane to the essential exclusion of oxygen; (b) continuously supplying gas feed to a bottom portion of said reactor at a rate sufficient to increase the concentration of microorganisms, said gas feed comprising said gas substrate being supplied to a bottom portion of said reactor via at least one injector using a motive liquid to form microbubbles having a diameter of less than about 500 microns; and (c) operating in substantially a liquid retention mode until the concentration of microorganisms is between 3 and 500 times that in step (b).

17. The process of claim 16 wherein the reactor is a bubble column reactor.

18. The process of claim 16 wherein the reactor is a liquid mixed reactor.

19. The process of claim 16 wherein the concentration of the oxygenated organic compound in the aqueous menstruum is maintained below that which unduly adversely affects the rate of growth of the culture of microorganisms.

20. The process of claim 16 wherein at the initiation of the start-up, the gas feed is supplied as bubbles in the range of 100 to 5000 microns in diameter.

* * * * *